US008494646B2

(12) United States Patent
Weiss et al.

(10) Patent No.: US 8,494,646 B2
(45) Date of Patent: Jul. 23, 2013

(54) IMPLANTABLE DEVICE (75) Inventors: Ingo Weiss, Berlin (DE); Stefan Knorr, Berlin (DE); Michael Diebold, Berlin (DE); Stephan Fandrey, Affoltern am Albis (CH)

(73) Assignee: Biotronik SE & Co. KG, Berlin (DE)

( * ) Notice: Subject to any disclaimer, the term of this patent is extended or adjusted under 35 U.S.C. 154(b) by 50 days.

(21) Appl. No.: 13/330,109

(22) Filed: Dec. 19, 2011

(65) Prior Publication Data

US 2012/0158097 A1    Jun. 21, 2012

Related U.S. Application Data (60) Provisional application No. 61/425,255, filed on Dec. 21, 2010.

(51) Int. Cl.
*A61N 1/00* (2006.01)
(52) U.S. Cl.
USPC ............................................................ 607/59
(58) Field of Classification Search
USPC ............................ 607/59, 116, 122; 320/116
See application file for complete search history.

(56) References Cited

U.S. PATENT DOCUMENTS

| 7,127,294 B1 | 10/2006 | Wang et al. |
| 2005/0283213 A1 | 12/2005 | Gray |
| 2006/0267551 A1* | 11/2006 | Sutardja ........................ 320/116 |
| 2008/0154348 A1 | 6/2008 | Atalar et al. |
| 2010/0114211 A1 | 5/2010 | Donofrio et al. |
| 2010/0114258 A1 | 5/2010 | Donofrio et al. |

FOREIGN PATENT DOCUMENTS

EP    2 067 501 A2    10/2009

OTHER PUBLICATIONS

European Search Report dated Aug. 8, 2012, 16 pages.
European Search Report dated Mar. 22, 2012, 6 pages.

* cited by examiner

*Primary Examiner* — George Manuel
*Assistant Examiner* — Robert N Wieland
(74) *Attorney, Agent, or Firm* — ARC IP Law, PC; Joseph J. Mayo (57) ABSTRACT

An implantable medical device having at least one functional lead which extends longitudinally, wherein the functional lead is connected to an electrode pole for the purpose of discharging therapeutic signals or detecting diagnostic signals, wherein the functional lead has a current limiting device in one longitudinal section, wherein the current limiting device has a first and a second current limiter which are switched in parallel, and wherein each current limiter is configured to prevent electrical current in the electrical lead from exceeding a pre-specified maximum value.

15 Claims, 7 Drawing Sheets

Fig. 9B

IMPLANTABLE DEVICE

This application claims the benefit of U.S. Provisional Patent Application 61/425,255 filed on 21 Dec. 2010, the specification of which is hereby incorporated herein by reference.

BACKGROUND OF THE INVENTION

1. Field of the Invention

At least one embodiment of the invention relates to a permanently or temporarily implantable medical device having an electrical lead that extends longitudinally.

2. Description of the Related Art

Such devices, for example electrode leads for electrical stimulation, have the disadvantage that the electrical conductors thereof can heat up in an MRI machine, because the alternating magnetic fields in an MRI machine induce electrical currents in the electrical conductor that are not insignificant. For this reason, patients with heart pace makers usually cannot be examined in an MRI machine at the current time, or can only be examined in a limited manner.

Implantable heart pacemakers or defibrillators typically have at least one stimulation electrode lead attached to said pacemaker, wherein said electrode lead has a standardized electrical connection at its proximal end, said end being provided for connection to the heart pace maker or defibrillator, and wherein said electrode lead has one or multiple electrode poles on it distal end, said distal end being provided for actively locating the same in the heart. Such an electrode pole serves to release an electrical impulse, for instance to the (myocardial) tissue of the heart, or to sense electrical fields in order to be able to sense an activity, such as heart activity.

For this purpose, electrode poles typically form electrically conductive surface sections of an electrode lead. Electrode poles are typically provided in the form of a ring around the electrode lead, or in the form of a point or tip electrode at the distal end of the electrode lead.

The electrode poles are connected to contacts of the electrical connection of the electrode lead on the proximal ends thereof, in an electrically-conducting manner via one or multiple electrical conductors. Consequently, one or multiple electrical leads, which electrically connect one or multiple electrode poles to one or multiple contacts, run between the contacts of the electrical connection of the electrode leads at the proximal end thereof and the electrode poles at the distal end thereof. These electrical leads can be used to both transmit stimulation impulses to the electrode poles and also to transmit electrical signals obtained by means of the electrode poles to the proximal end of the electrode lead. In the following description, said electrical leads are also characterized as functional leads.

Such functional leads are electrical leads which are necessary for the functions of each electrode lead. As such, they are subject to the danger that electrical current can be induced in them by external alternating magnetic fields. This electrical current can, for instance, lead to an undesirable heating of the functional leads or of the electrode poles connected to the same, or can lead to a discharge of corresponding current via the electrode poles into the surrounding tissue, thereby heating the surrounding tissue.

The use of a diode to limit current in an electrode conductor is known from EP 2 067 501 A2. The solution has the advantage that it functions substantially independently of the interference frequency and the current induced by the same. However, the relatively high voltages to which a diode is exposed, particularly under high-performance conditions in a magnetic resonance imager with interfering alternating magnetic fields, the diode being switched into the circuit in the blocking direction, can lead to destruction of the diode. As a consequence, the diode ceases to conduct current. In a heart pace maker or a defibrillator, this leads to loss of the therapeutic or diagnostic function of an electrode pole, which becomes uncoupled from the control device due to the destroyed and therefore non-conducting diode.

The known solution mentioned above is also sensitive to mechanical stress. This is because semiconductors are very fragile by nature, and must be connected to metal contacts via a bond which is likewise mechanically susceptible.

BRIEF SUMMARY OF THE INVENTION

The problem addressed by at least one embodiment of the invention is that of creating a medical device which solves or mitigates the problem described above.

According to at least one embodiment of the invention, this problem is solved by a permanently or temporarily implantable medical device having a functional electrical lead which extends longitudinally, wherein said functional lead is connected on the distal end thereof to an electrode pole for the purpose of discharging therapeutic signals or detecting diagnostic signals, and wherein said functional lead has a current limiting device in one longitudinal section, said device having a first and a second current limiter switched in parallel. Each current limiter is designed to prevent electrical current in the electrical lead from exceeding a pre-specified maximum value.

According to at least one embodiment of the invention, the second current limiter is further designed to allow a pre-specified minimum value of the electrical current strength, said strength being necessary for the practical operation of the device, in a second current branch of the parallel circuit, the second current branch being parallel to the first current branch and containing only the second of the two current limiters, in cases where an electrical operating voltage is present simultaneously with the electrical current strength being lower than a pre-specified minimum value in a first current branch of the parallel circuit, said first current branch containing only the first current limiter.

The solution according to at least one embodiment of the invention enables current to flow in the functional electric lead to the electrode pole, even in the event that the first current limiter loses its electrical conductivity due to a malfunction, such that a current flowing through the electrode pole into the tissue is sufficient for the therapeutic or diagnostic function of the device. At the same time, the flow of current is sufficiently limited by the function of the second current limiter that a potential heating is prevented to the greatest degree possible, said heating being possible by means of, for example, induction caused by interference fields.

The largely fragile implementation of a current limiter is supplemented by the parallel switching of two current limiters provided according to the invention, the same adding a safety path formed by the aforementioned second current branch. In preferred examples, this can be designed as a mechanically robust feature, as described in greater detail below.

Embodiments of the invention are described in the following. The additional features of the embodiment examples can be combined with each other to form further embodiments in instances where those alternatives are not expressly described as being exclusive to each other.

The first current limiter is preferably designed to block the first current branch when a blocking voltage of a defined polarity and amplitude is present at the first current limiter.

In various alternative embodiments, the electrical conductivity of the first current limiter is dependent either on a frequency of an alternating field to which the first current branch is exposed, or on an electrical voltage falling on the first current branch, or on a magnitude or a direction of an electric or magnetic field to which the first current branch is exposed, or on a temperature at the first current branch, or on a combination of at least two of the variables above.

Preferred embodiments of the invention contain, as the first current limiter, at least one diode or at least one transistor, or a circuit having at least one diode and at least one transistor. Suitable options for the transistor include, in alternative embodiments, a junction gate field effect transistor, JFET for short, a metal semiconductor field effect transistor, MESFET for short, a field effect transistor with high electron movement, HEMT for short, particularly a pseudomorphic HEMT, pHEMT for short, or a metal oxide semiconductor field effect transistor, MOSFET for short. In one variant, the first current limiter is formed by two transistors switched in series, the gate electrodes of the same being connected directly to each other.

The first current limiter is preferably designed as a monolithically integrated semiconductor component. As such, the same can be embodied in the form of a hollow cylinder having contact surfaces at is ring-shaped longitudinal ends. The hollow cylinder surrounds the functional lead and, if a device having segments of varying conductivity is present, the hollow cylinder surrounds the longitudinal section having lower electrical conductivity.

In one embodiment, the functional lead has a connection device on a proximal end of its longitudinal extension, to connect to a control device of the medical device. On an opposite, distal end of its longitudinal extension, the functional lead has at least one electrode pole which is suitable for discharging electrical stimulation impulses to stimulatable biological tissues, wherein the current limiting device is arranged near to the distal end of the lead.

The current limiting device is preferably located at most 5 cm away from the electrode pole along the longitudinal extension of the lead.

In one embodiment, the functional lead is connected to bridge contacts which are arranged on both sides of the current limiting device in the longitudinal direction, and which are designed to be directly connected to each other by means of connection to a bridging device.

One embodiment additionally has a control device which is connected to the functional lead, said control device having:
- a measuring unit which is designed to determine a measured value from the varying strength of electric current in the lead by means of a sensor. Said measuring unit is suitable for providing an indication that an electric current strength in the lead has exceeded the maximum value.
- an analysis unit which is designed to detect an event where an electric current strength exceeds the maximum value, utilizing the measured value, and optionally to generate a control signal, and
- a switch unit which is connected to the control device and to the first current limiter, and which is designed to produce a blocking voltage upon the presence of the control signal in the circuit, said blocking voltage being suitable for blocking the first current branch leading through the first current limiter, impressing said blocking voltage on the functional lead.

Such a medical device preferably has a therapeutic unit in its control device, said therapeutic unit being connected to the analysis unit and being designed:
- to produce electrical stimulation impulses having a pre-specified temporal progression of the amplitude thereof, said impulses creating a pre-specified target value of the electrical current strength in the functional lead. Said target value is larger than the minimum value and smaller than the maximum value.
- to discharge said stimulation impulses via the functional lead to the external environment, and
- to modify the temporal progression of the stimulation impulse amplitude in the functional lead in the event that the control signal produced by the analysis unit is present.

To ensure successful therapy, as an additional safeguard to the foregoing features, the medical device also preferably has a feedback path which can be adjusted according to the therapeutic parameters to ensure safety of the patient in all cases. In one embodiment, the measuring unit is additionally designed to detect an updated value of a parameter which is suitable for displaying the efficacy or lack of efficacy of stimulation impulses discharged into the tissue intended to be stimulated, wherein
- the analysis unit is designed to detect the efficacy or lack of efficacy of the discharged stimulation impulses by utilizing the updated values and pre-specified criteria, and
- the therapeutic unit is designed to modify the temporal progression of the stimulation impulse amplitude in the functional lead in the event that a lack of efficacy is detected.

The sensor is preferably arranged on the functional lead and connected to the analysis unit via the second signal path.

In addition, for the purpose of communication between the device and an external monitoring device, a communication unit can be provided in the medical device, the communication unit being connected to the analysis unit, and the communication occurring via a communication channel. The communication unit is designed, when the control signal is present, to signal the monitoring device on the same communication channel that an electrical current strength is present in the functional lead which exceeds the maximum value.

In addition to the embodiments described herein other alternative embodiments may include some or all of the disclosed features.

BRIEF DESCRIPTION OF THE DRAWINGS

Further embodiments are explained in the following with reference to the figures. The following figures show.

DETAILED DESCRIPTION OF THE INVENTION

Figure 1:
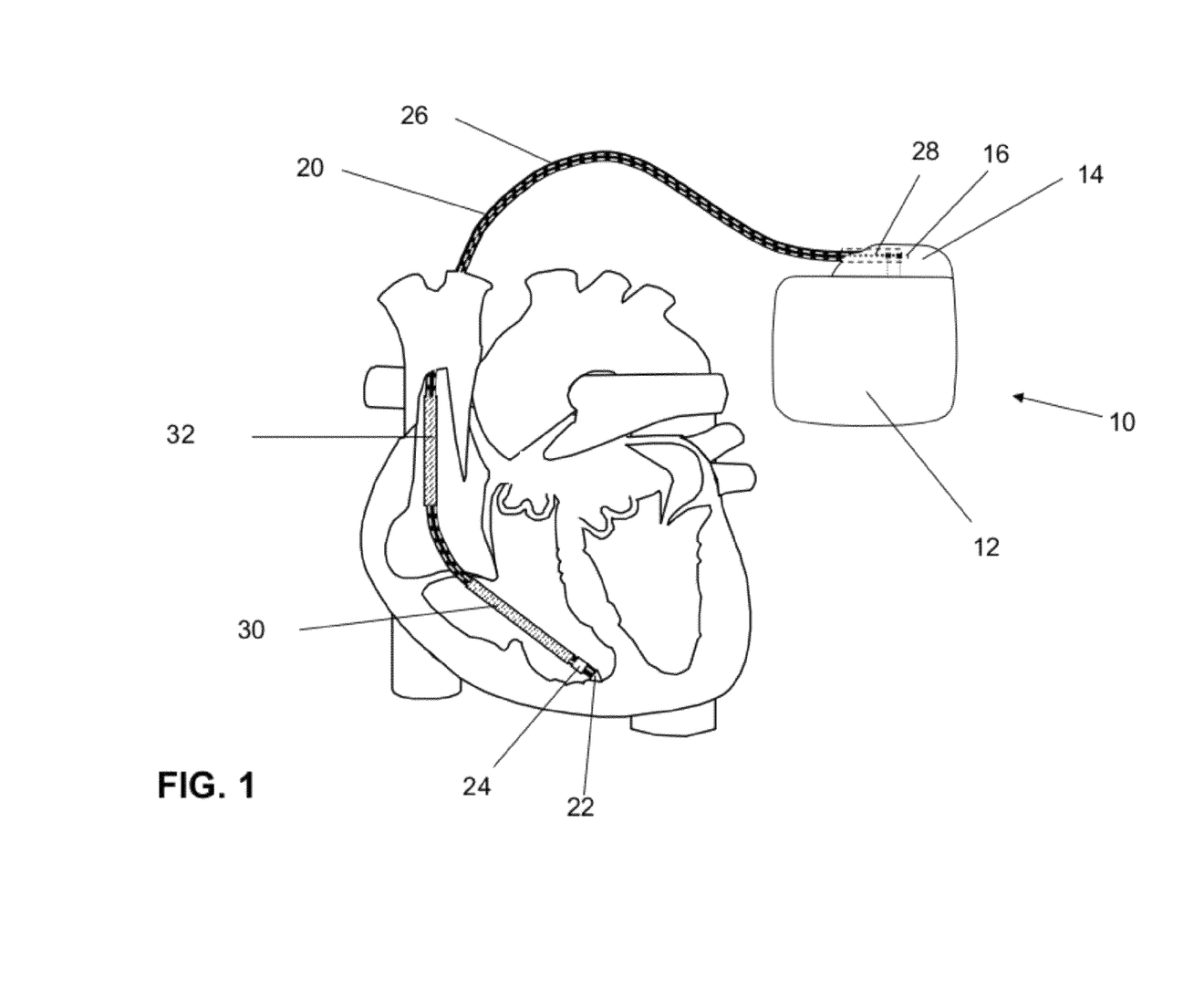
FIG. 1 an embodiment of the invention, in the form of a heart pace maker.

FIG. 1 shows, as an example of implantable medical devices, an implantable heart stimulator 10 and an implantable electrode conductor 20 connected to the same.

The implantable heart stimulator 10 can be a heart pace maker or a cardioverter/defibrillator (ICD). In the illustrated embodiment, the heart stimulator 10 is a ventricular heart pace maker and defibrillator. Other known heart stimulators are two-chamber heart pace makers designed to stimulate the right atrium and the right ventricle, or biventricular heart pace makers which can stimulate the left ventricle in addition to the right ventricle.

Such stimulators typically have a housing 12, which usually is made of metal, and is consequently electrically conducting and can serve as a large-surface area electrode pole. Typically, a connection housing 14 is attached to the outer side of the housing, and is also called a 'header'. Such a header typically has contact connectors as receptacles for plug contacts. The contact connectors have electrical contacts 16 which are connected via appropriate conductors to the electronics arranged inside the housing 12 of the heart stimulator.

The electrode conductor 20 likewise constitutes an implantable medical device in the sense of this invention. Electrode poles, in the form of a point or tip electrode 22, as well as one ring electrode 24 arranged near said electrode poles, are arranged at the distal end of the electrode conductor 20 in a conventional manner. The electrode poles 22 and 24 are designed in such a manner that they serve to sense electrical potentials of the heart tissue (myocardial), or they serve to discharge electrical signals, for instance to release stimulation impulses to the heart tissue surrounding the electrodes, according to the function of the heart stimulator to which the electrode conductor 20 is attached. FIG. 1 shows how the electrode poles, that is, the tip electrode 22 and the ring electrode 24, and in certain cases the electrode conductor 20, are located in the apex of a right ventricle of a heart.

Both the tip electrode 22 and the ring electrode 24 are electrically connected to a plug contact 28 at the proximal end of the electrode conductor 20 via at least one electrical lead 26 each. The plug contact 28 has electrical contacts which correspond to the electrical contacts 16 of the contact connector in the connection housing 14 of the implantable heart stimulator.

As described in greater detail below, the electrical leads 26 in the electrode conductor 20 can be constructed in different longitudinal sections as nearly straight feed cables or as helix-shaped coiled leads. Such leads, which connect the functional electrode poles with electrical contacts of the plug contact on the proximal end of the electrode conductor 20 in an electrically conducting manner, are also characterized in the scope of this description as functional leads because they transmit therapeutic electric signals from the plug contact to one or both electrode poles, or they convey sensed electrical potentials representing signals from one or both electrode poles to the plug contact. Consequently, said leads serve to fulfill the elementary function of the medical device.

The functional electrical leads 26, which connect the electrode pole 22 and/or 24 to the electrical contacts of the plug 28 of the electrode conductor 20, are enclosed over the majority of their length by an insulating sheathing, such that electrical contact to the tissue of the heart occurs in a targeted manner at the electrode poles.

In addition to the electrode poles 22 and 24, which typically serve to stimulate the heart tissue (in this case, ventricular tissue), the electrode lead 20 also has two additional large surface area electrode poles 30 and 32, which function as defibrillation electrodes and are formed by at least one uninsulated helix-shaped coiled wire.

Readers should note that the invention is explicated using this embodiment and in the form of a right ventricular heart pace maker and defibrillator. However, in principle, an ablation electrode lead could also be adduced as an example of a medical device in the sense of the invention, said ablation electrode lead likewise projecting into the heart of a patient and being controlled by a device outside the patient's body and, for that purpose, connected to the same. Furthermore, such electrode leads can also function in other applications, upon technical adjustment for the special requirements of other specific uses to stimulate tissue or relay signals to/from nerves, the brain, and other organs, or as feeds from implantable sensors.

Figures 2, 3:
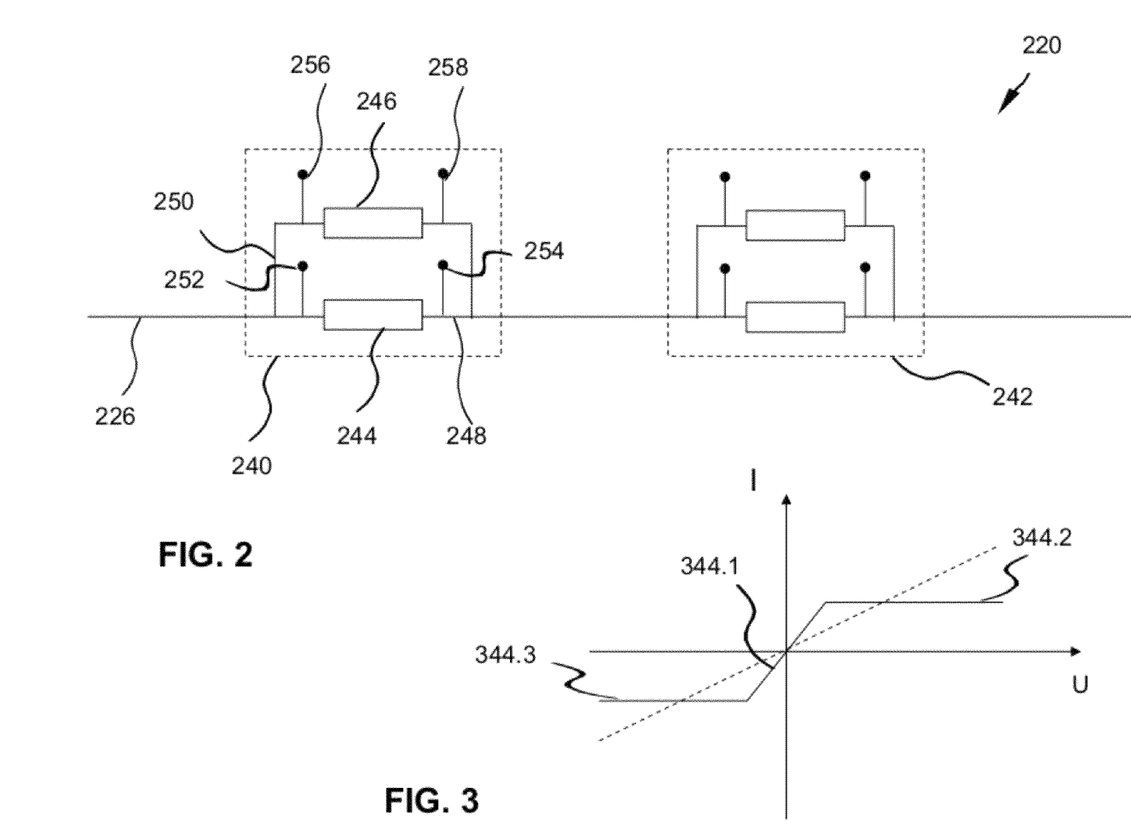
FIG. 2 a simplified circuit diagram of one embodiment of an electrode lead.
FIG. 3 a current voltage curve for the application of a current limiter suitable for the example illustrated by FIG. 2, given with reference to a resistance curve showing Ohm's Law.

FIG. 2 is a simplified circuit diagram of one embodiment of an electrode conductor. In parallel, reference is made to FIG. 3, which shows a characteristic curve of the current limiter.

The electrode conductor 220 of the present embodiment contains one (or multiple) functional leads 226. The functional lead 226 serves to transmit therapeutic and diagnostic signals between electrode poles arranged at the distal end of the conductor, the same being identified by the reference numbers 30 and 32 in FIG. 1, and the plug contact 28 at the proximal end of the electrode conductor 220. A longitudinal section of the functional lead 226 is illustrated, in which two current limiting devices 240 and 242 are arranged. Both current limiting devices 240 and 242 are connected to each other in series via the functional lead 226. The internal construction of the current limiting devices 240 and 242 is identical. For this reason, and to reduce space here, the following only describes in detail the construction of the current limiting device 240. The number of the present current limiting devices can be varied according to need. In contrast to the example illustrated in FIG. 2, only one current limiting device can also be provided. Alternatively, it is possible to provide more than two current limiting devices, according to the intended application.

The current limiting device 240 includes a first current limiter 244 and a second current limiter 246 which are switched in parallel. Both current limiters 244 and 246 primarily serve to prevent the electrical current strength in the functional lead from exceeding a pre-specified maximum value. The first and second current limiters 244 and 246 can be realized for the purposes of the present embodiment are described with respect to FIG. 6 to FIG. 9 below. Due to the aforementioned parallel switching of the first and the second current limiters, two current branches 248 and 250 are present. The first current branch 248 is routed between the proximal and the distal ends of the functional lead 226, through the first current limiter 244. The second current branch 250 is routed through the second current limiter 246. Both current branches 248 and 250 can be bridged. For this purpose, accessible contact bridges 252 and 254 are provided in the first current branch, and contact bridges 256 and 258 are accessible in the second current branch 250. The functionality of the current limiting device is explained in more detail in the following. Generally speaking, the capability of the first current limiter 244 to conduct electricity is dependent on one parameter. As an example, in the case of induction of electrical current in a magnetic field, as for example created by a magnetic resonance imager, temporal variation of a magnetic flux that permeates a circuit containing the functional lead will effect an induction voltage, which in turn creates induction current in the functional lead. The speed of change, i.e. the temporal deviation of the magnetic flux, determines the amount of induction voltage, and consequently, via the known physical relationship between the two, also the strength of the induced current. In the case of an alternating magnetic field, of the high frequency which is typical for magnetic resonance tomography, the effective value of the induced current leads to heating of the functional lead, which can be damaging particularly in the area of the electrode poles (not illustrated in FIG. 2). The high frequency field of a magnetic resonance imager is typically pulsed with a duty factor of well under 10%. However peak values can be very high.

The current spikes induced thereby are removed by means of the current limiter 244, which typically has the characteristic curve 344 illustrated in FIG. 3. The characteristic curve 344 has a linear region 344.1 in which the strength of current is approximately proportional to the voltage. At both ends of said linear section, i.e. at both higher positive and higher negative voltages, saturation regions occur in which the strength of the current is substantially constant when voltage increases further. As a comparison, a dashed line in FIG. 3 illustrates a resistance curve showing Ohm's Law, said curve showing a linear dependency of the current strength across the entire voltage range illustrated in the figure.

The therapeutic current which is necessary during normal operation should lie within the linear region 344.1 of the characteristic curve of the current limiter 244. That is, the current should always vary in a range below the threshold of the current limiting function.

The second current limiter 246 in the second current branch 250 of the current limiting device 240 is similarly embodied like the first current limiter 244 with respect to its fundamental functionality. However, the second current limiter is designed to substitute for the function of the first current limiter 244 in the case that the same loses conductivity for electrical current. This situation is typically characterized in that the strength of electrical current falls to lower than a pre-specified minimum value in the first current branch of the current limiting device, when operating voltage is applied. The pre-specified minimum value is determined by the conditions necessary for therapeutic function of the device, for example a strength of current which is sufficient to achieve the desired therapeutic effect. In general, the current strength which can be attained in the functional lead must at least reach the minimum value for the device to be operated according to its practical function. The second current limiter 246 ensures that in such a case where the first current limiter fails, current can still flow in the functional lead 226, said current at least reaching the pre-specified minimum value.

Due to the design, wherein both current limiters 244 and 246 are switched in the circuit in parallel, the threshold value of the current strength, which is used to determine the current-limiting function of the system, must be given a smaller value for both current limiters 244 and 246 compared to a system having a current limiting device which only includes one current limiter. In the event that the current limiter 244 fails, the entirety of the current is conducted through the functional lead via the second current limiter 246. The current strength which can be attained in this case with a pre-specified operating voltage, which is intended for cases where the current limiting device is fully intact, will be smaller. This is due to the higher resistance of the second current limiter 246 with respect to the parallel switching of the first and the second current limiters 244, 246. The second current limiter 246 is designed in such a manner that the current strength attainable in this case always enables the necessary minimum current strength to be applied to the functional lead 226 for the proper operation of the medical device.

Contact bridges 252 and 254 for the first current branch, and contact bridges 246, 258 for the second current branch serve to provide a bridging option for one or even both current limiters in the event of a potential failure. In this way, in the event that one of the current limiting devices 240 has a defect, the functional lead 226 can be repaired for continued use for therapeutic or diagnostic purposes. With only one bridging connection, utilizing a short circuit, the current-limiting function of the device is lost. However, this saves the patient the otherwise necessary operation to implant a new electrode conductor. Such measures for bridging can namely be carried out with the device in the implanted state, or as an alternative, in a minimally invasive manner. In a minimally invasive repair, the contact bridges 252 and 254 or 256 and 258 are connected to each other. In this process, they can be connected to each other by, for example, electrical breakdown or by piezo welding. As an alternative, a repair can be carried out in which a shunt is inserted to bridge the affected current limiter, by means of a stylet. Such a shunt can be produced using, for example, a wax which slides easily. This likewise has the advantage of providing protection from overheating in the event of high induced current, because the wax melts upon overheating, thereby breaking the electrical connection between the affected contacts.

Figure 4:
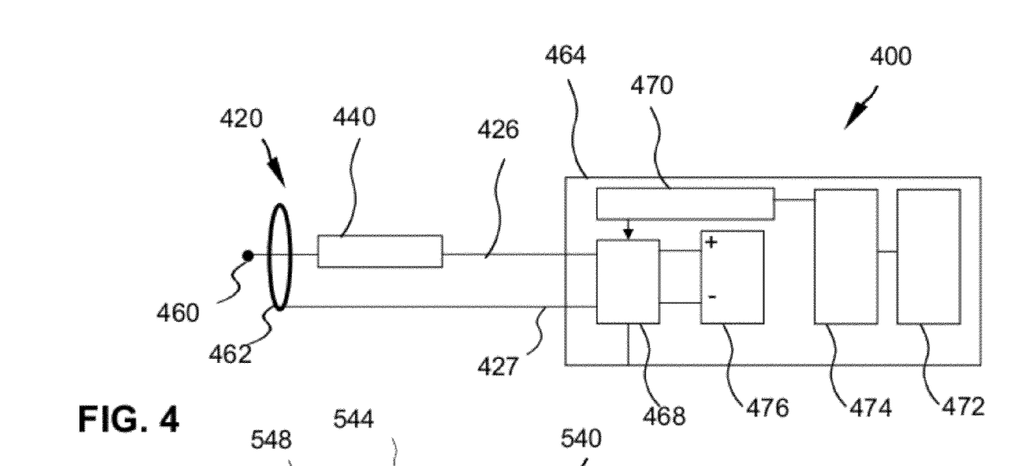
FIG. 4 a simplified circuit diagram of an electrode lead according to the further embodiment.

FIG. 4 is a simplified circuit diagram of an electrode conductor according to a further embodiment. A heart pace maker 400, which forms an active implant, is connected to an electrode conductor 420. The electrode conductor includes functional leads 426 and 427. The functional lead 426 connects a control device 464 of the heart pace maker 400 to a tip electrode pole 460. A second functional lead 427 connects the control device 464 to a ring electrode pole 462. The functional lead 426 is connected to a current limiting device 440. It is practical to arrange the current limiting device near to the distal tip electrode pole 460, for example at a distance of less than 5 cm measured along the longitudinal dimension of the functional lead 426. In this way, undesired heating of the electrode pole resulting from the influx of high frequency alternating magnetic fields can be particularly efficaciously repressed. This is the case regardless of the shape and form of the electrode pole; that is, it is independent of, for example, whether the electrode pole is a ring electrode or a tip electrode. The functional leads 426 and 427 are connected to a switch unit 468. The switch unit is controlled by a control unit 470 of the control device 464. The control unit 470 is connected on the input side of the same to a measuring unit 472 and to an analysis unit 474. The measuring unit 472 has a sensor which is not illustrated in detail and with which the measuring unit detects an updated value of a parameter. The parameter is suitable for indicating functionality or failure in the functional electrode poles 460 and 462 in the current operation state. Particularly, the parameter is suitable for displaying the efficacy or failure of stimulation impulses which are discharged into the tissue intended to be stimulated.

Radio frequency pulses can be detected, for example, by a rotational field coupled into a radio frequency antenna, or a gradient/alternating field coupled into a communication coil, or by an optocoupler which converts the induced current into optical signals.

An analysis unit 472 which is switched downstream detects the efficacy or lack of efficacy of operation of the functional electrode poles 460 and 462 at the time, by utilizing the updated parameter values and pre-specified criteria, i.e., whether the stimulation impulses have the desired effect on the surrounding tissue. Corresponding information is broadcast to the control unit 470.

An energy supply 476 supplies the control device 464 with the energy required during operation, and likewise produces the energy required for the discharge of stimulation impulses via the switching unit 468.

One possible implementation of the current limiting device 440 is described in more detail in the following. A diode, particularly a PIN diode, initially is suited for use as the current limiter in the current limiting device. The diode is connected in such a manner that the arrangement does not influence the discharge of stimulation impulses during normal operation with the polarity intended for the same. Particularly, stimulation impulses provide stimulation with the correct polarity. Upon detection of an event which results in the inefficacy of the stimulation impulses, particularly upon detection of a high frequency alternating magnetic field by means of the measuring unit 472 and the analysis unit 444, the control unit 470 effects the application of a blocking voltage to the PIN diode of the current limiting device. The switching unit 468 is appropriately controlled for this purpose. The PIN diode of the current limiting device 440 blocks and in this way prevents the flow of current, having a current strength, through the functional lead, wherein said current strength would negatively influence the efficacy of therapeutic stimulation impulses. In order to achieve a blocking bias voltage, the required counter pole is coupled to the surrounding tissue via a housing of the control device 464 or another electrode pole, such as the ring electrode pole 462 for example, when the device is in the implanted state.

The second current limiter, arranged in parallel, of the current limiting device 440 can, but must not necessarily, be a PIN diode. It is advantageous if a passive path is implemented instead of an additional PIN diode, e.g. a resistor, a device, or a material which offers resistance. The resistance serves as a safety path via which a stimulation can be carried out, albeit with higher energy consumption. The resistor should be selected in such a manner that it offers sufficient MR protection, preferably 500 Ohms, or in the case of multiple such circuits along the electrode conductor, a total of preferably 1000 Ohms or more.

In an alternative option for realizing the device, the blocking bias voltage at the PIN diode of the current limiting device 440 is present as a default, and is only briefly switched off when a stimulation impulse is generated. This can occur automatically by means of reversion of polarity at the current supply connection. It should be noted in this embodiment, that the leakage voltage through the PIN diode must be reliably low.

Figure 5A:
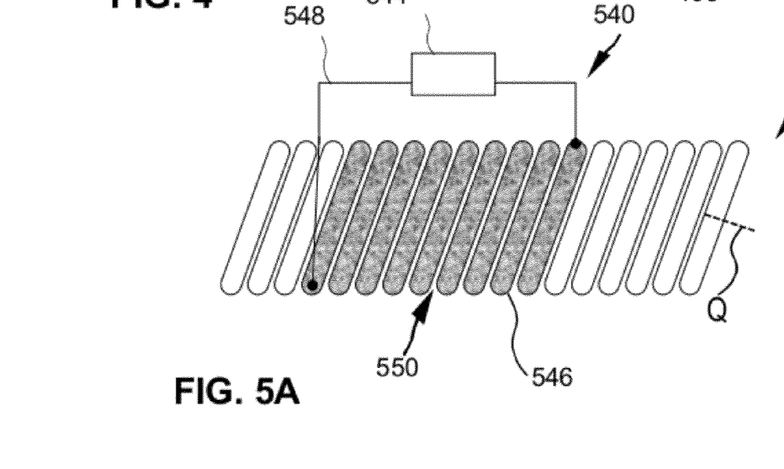
FIGS. 5A and 5B a schematic illustration of an electrode conductor given in a side view and in a cross-sectional view, to explicate a further embodiment.
Figure 5B:
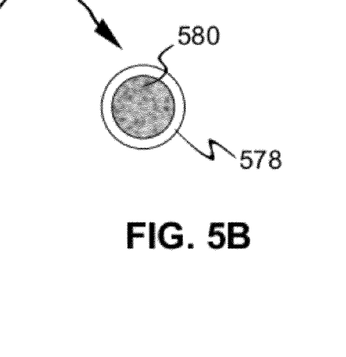

FIGS. 5A and 5B show a schematic illustration of an electrode conductor given in a side view and in a cross-sectional view, to explicate a further embodiment. In this embodiment, a current limiting device 540 is realized in a functional lead 526 by utilizing a special design of the functional lead itself. To serve this description, initially a cross sectional view of the lead is explained with reference to FIG. 5B, the plane of the cross sectional cut being indicated by a dotted line Q in FIG. 5A. The functional lead is realized by the spiral-shaped coiled lead, having a core 300 which is a poor electrical conductor, said core being characterized by a high mechanical robustness with respect to the mechanical loads occurring during operation. The core is represented in FIG. 5B by an illustrated texture. The core is surrounded by a coating 578 which is a good electrical conductor. The current which is transported through the lead of the functional lead 526 is routed primarily through the coating 578 due to the differing electrical conductivities of the core 580 and coating 578. To realize the current limiting device 540, the coating 578 with good conductivity is removed in a longitudinal section of the functional lead 526. The functional lead 526 forms, in this longitudinal section indicated in FIG. 5A by a corresponding texture, a relatively high resistance segment. This longitudinal section of the functional lead forms the second current branch 550 in the present embodiment, corresponding to the second current branch 250 in FIG. 2. The second current branch 550 is bridged with low resistance by means of a contact of the functional lead 526 in the area of the lead not having the coating 578. This forms a first current branch 548 which corresponds to the first current branch 248 in FIG. 2. This first current branch 548 includes a current limiter 544 which forms a low-resistance resistor for current strengths present during normal operation, that is, therapeutic or diagnostic operation. This resistor does not introduce any disruptive influences which raise the current strength in the functional lead 526.

The current branch 544 should merely provide a few mOhms of resistance, as long as it is operating in the range in which is does not function as a current limiter. The high-Ohm safety path 550 should lie in the range above 500 Ohms, preferably over 1.0 kOhms, in order to effectively dampen induced high frequency currents, and nevertheless ensure the functionality of the implant over a limited period of time.

Instead of the conductive coating 578, a different form of the sheathing possessing good electrical conductivity can be used. A coating with good electrical conductivity 578 has the advantage that it can be removed relatively easily. For example, it can be burned off in the desired longitudinal section during the manufacturing of the functional lead 526.

The present embodiment has the advantage that the contact can have a simple design while also realizing the parallel switching of the second current limiter. Due to the high resistance of the second current limiter 546, the same being formed by the functional lead itself, an operation of the device following failure of the first current branch 548 requires adjustment of the power or energy discharged to the functional lead 526, in order to produce therapeutic stimulation impulses with a power or energy which can be attained using the low-resistance first current branch. On this point, reference is made to the embodiment in FIG. 4, particularly to the control unit 470, which can control the switching device 468 during operation in order to achieve an appropriate adjustment of the electrical power or energy discharged to the functional lead 426 or 427.

Figure 6A:
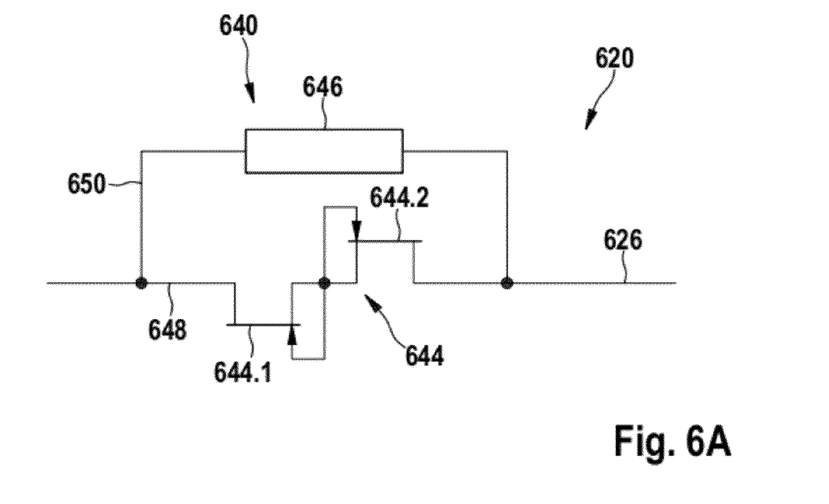
FIGS. 6A and 6B a circuit diagram and a schematic cross-sectional view of a current limiter according to one embodiment.
Figure 6B:
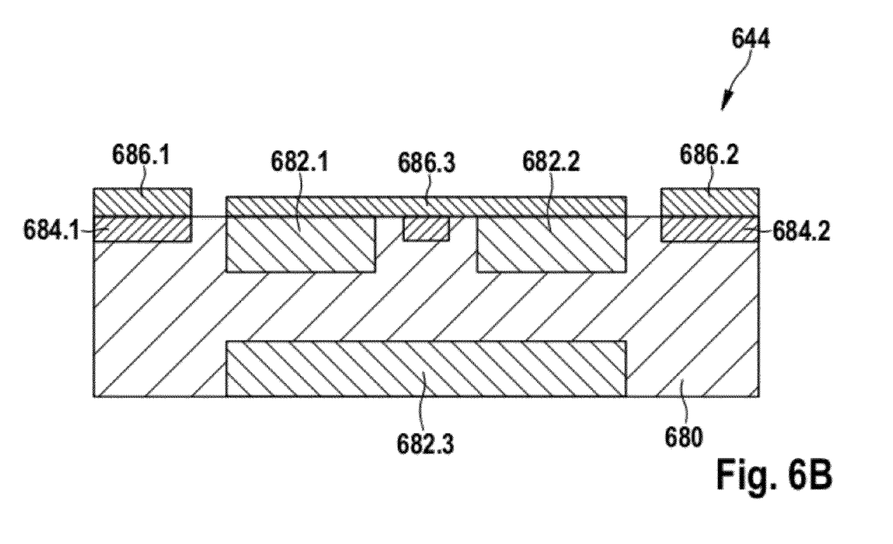

FIGS. 6A and 6B show a circuit diagram and a schematic cross sectional view of a current limiter according to one embodiment. The circuit diagram in FIG. 6A shows one longitudinal section of a functional lead 626, wherein a current limiting device 640 is provided in said longitudinal section. The current limiting device contains a first current limiter 644 in its first current branch, said current limiter consisting of two junction field effect transistors (JFET) switched in series. Both JFETs 644.1 and 644.2 are N channel JFETs in the present embodiment. They are coupled to each other on the source and gate connections thereof. Their drain connections form the connections on the input and output side to the first current branch 648. The second current branch 650 of the current limiting device 640 includes a current limiter 646. This can be formed by a high-resistance longitudinal section of the functional lead 626, for example—as illustrated in FIG. 5A. The switching of both JFETs 644.1 and 644.2 in the first current limiter 644 can be realized by utilizing secondary discrete transistor components. Alternatively, both JFETs 644.1 and 644.2 can be integrated into a single semiconductor chip. This is described in greater detail below with reference to FIG. 6B.

Instead of JFETs, the use of metal semiconductor field effect transistors (MESFETs), high electron movement field effect transistors (HEMTs), or metal oxide semiconductor field effect transistors (MOSFETs) is also possible. Particularly, MESFETs and HEMTs are characterized by an especially well-suited current limiting behavior at high frequencies, that is frequency ranges in which magnetic resonance imagers work. Typically, frequencies of the alternating fields generated by such devices lie in the range of 1 to 150 MHz. Pseudomorphic HEMTs, pHEMTs for short, are particularly well-suited HEMTs for this application. In this type of transistor, a two-dimensional electrode gas forms in a pseudomorphic thin semiconductor layer under tensile strain, which enables especially large energy gaps at the bottom edge of the conduction band in the transistor band structure. This enables increased conductivity in the transistor.

FIG. 6B shows a schematic cross sectional view of an integrated semiconductor component which implements the current limiter 644 in FIG. 6A. In a semiconductor substrate 680, which consists of an n-doped semiconductor material such as silicon or gallium arsenide for example, highly p-doped regions 682 are inserted into the matrix.

The region 682.3 can be applied to the bottom side of the substrate, or embedded in the substrate. In this case, it is important that the gap between 682.1/2 and 682.3 defines the channel width, which in addition to the doping determines the pinch off voltage Vp. This is a parameter with which the current limit can be set, in addition to the doping ratio of n and p+. This layer can also be embedded. In this case, the wafer (substrate) must necessarily be thinned such that no further current branch can form under the layer 682.3. Alternatively, a p-substrate can also be used in manufacturing, wherein the region 680 is n-doped, and the region 682.1/2 is p+ doped again afterwards.

N-doped regions 684.1 and 684.2 are embedded in the substrate with surfaces near to the highly doped regions 682.1 to 682.3 on both sides, and are provided with metal contacts 686.1 and 686.2. To control the channel between the highly doped regions 682.1 to 682.4, both highly doped regions 682.1 and 682.2 contact via a shared metal layer 686.3.

FIG. 6B can also be viewed as a geometric summary of the circuit in FIG. 6A. As such, the n+ doped region between 682.1 and 682.2 is the drain of the left transistor, and is the source of the right transistor. To clarify the functionality, the regions 684.1 and 684.2, and the region between 682.1 and 682.2 can be left out of the illustration. The n+ doping in this case only serves to improve the metal-semiconductor transition in the n-doped substrate, and prevents the formation of Shottkey diodes at the transition.

Figure 7A:
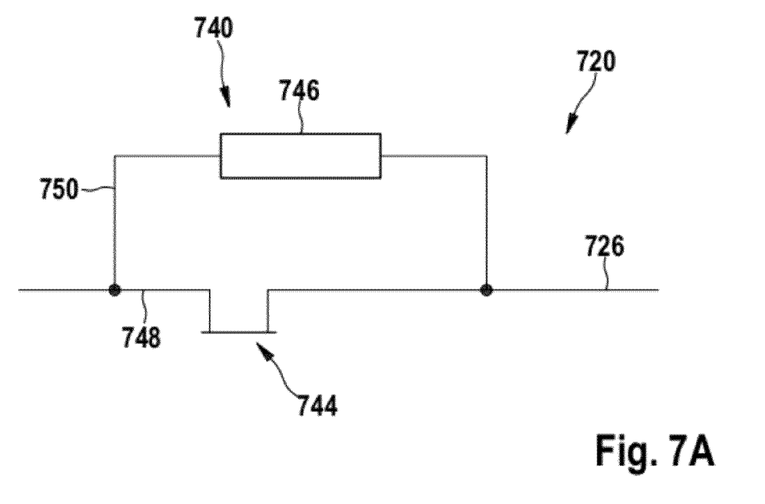
FIGS. 7A and 7B a circuit diagram and a schematic cross-sectional view of an alternative current limiter.
Figure 7B:
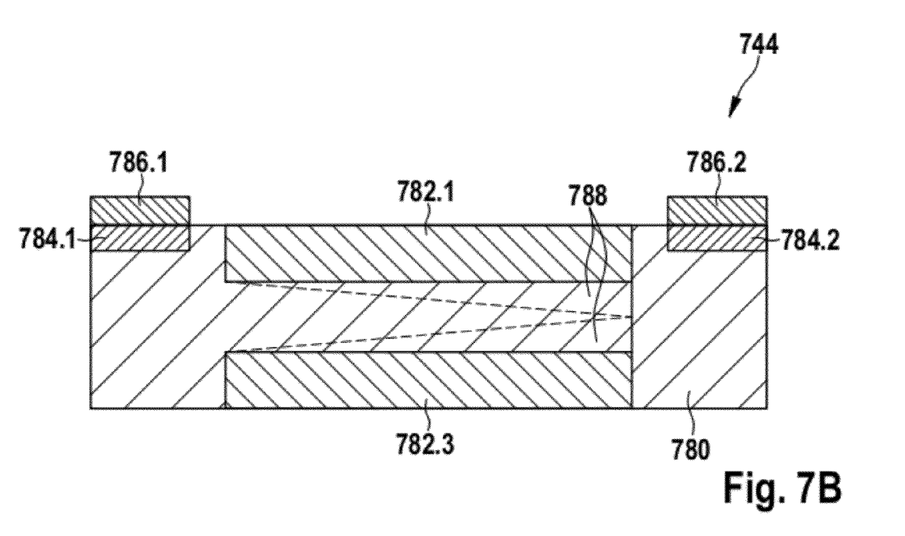

FIGS. 7A and 7B show a circuit diagram and a schematic cross sectional view of an alternative current limiter. The electrode conductor 720 shown in FIG. 7A has a current limiting device 740 in it functional lead 726. This differs from the current limiting device 640 in FIG. 6A in that the first current limiter 744 consists of only one single JFET in the present embodiment. The JFET 744 is operated with an open gate connection, and has a symmetrical construction which is described in greater detail below with reference to FIG. 7B.

The schematic cross sectional view of the JFET 744 serving as a current limiter is fundamentally similar to the structure of the current limiter 644 in FIG. 6B. However, the highly doped regions 682.1 and 682.2 are united in the present embodiment into one single region 782.1. The depletion layer 788 appearing during operation is represented in FIG. 7B in the semiconductor substrate 780 by a dashed line. Due to the symmetrical construction of this component, the channel constriction 788 works in both directions of current flow between the contacts 786.1 and 786.2. This results in a characteristic curve of the current limiter 744 as illustrated in FIG. 3 by the regions 344.1 to 344.3.

Figure 8:
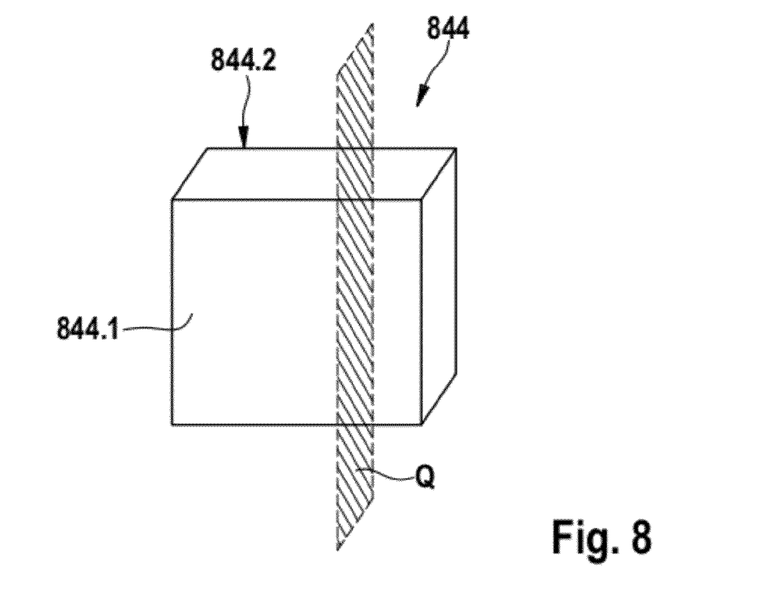
FIG. 8 a schematic three-dimensional illustration of a current limiter.

FIG. 8 shows a current limiter 844 in a schematic three dimensional view. The current limiter 844 is embodied as a cuboid shape semiconductor component which is coated on a frontal surface 844.1 and on a rear surface 844.2 with a metal layer to serve as a contact, wherein said rear surface 844.2 is not visible in FIG. 8 and is opposite the frontal surface 844.1. The internal construction of such a component is described below with reference to FIG. 9B.

Figure 9A:
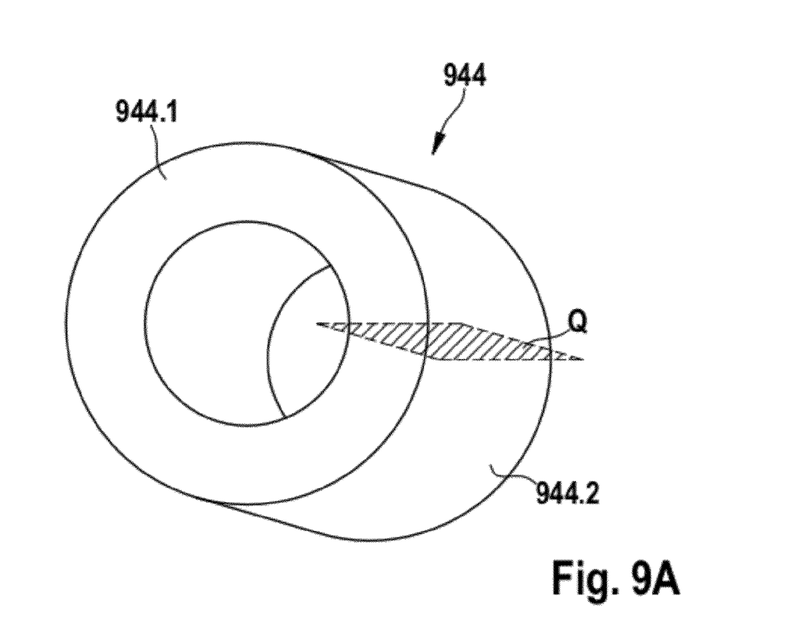
FIG. 9A a schematic three-dimensional illustration of an alternative embodiment of a current limiter.
Figure 9B:
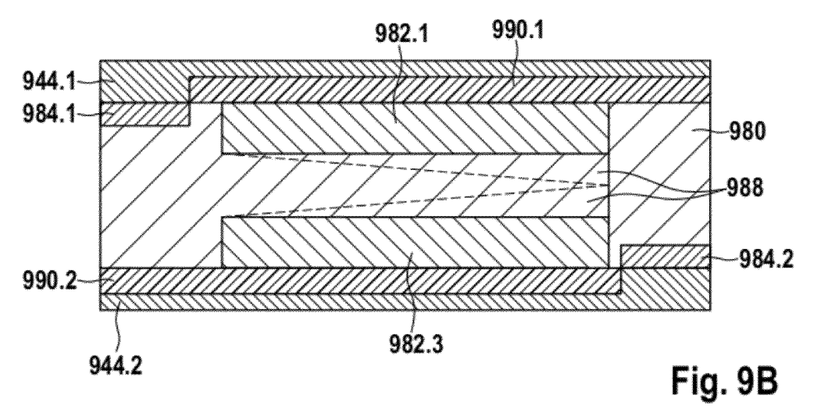
FIG. 9B a cross-sectional view of an additional embodiment of a current limiter according to FIG. 8 or 9A.

FIG. 9A initially shows an alternative embodiment of a current limiter 944, having a largely cylindrical shape. A ring-shaped component region 944.1 surrounds a circle-shaped opening 944.2. The component region is coated on its ring-shaped frontal side and on its ring-shaped back side with a metal to form a contact. FIG. 9B shows a cross sectional view which illustrates the construction of the current limiters 844 and 944 in the plane Q of the cross sectional cut. The construction substantially corresponds to the structure of the current limiter 744 in FIG. 7B. For this reason, the following only deals with the differences appearing in this structure. For the purpose of better embedding the component into a particularly spiral-shaped functional lead, the front-side metal surface 944.1 is connected to the input-side n-doped region 984.1. A layer of insulation 990.1 separates the metal contact from the highly-doped region 982.1. A corresponding construction shows the rear-side metal surface 944.2, which is separated from the highly doped region 982.3 by a layer of insulation 990.2, and which contacts the n-doped region 984.2 outside this region.

The embodiment in FIG. 9A has the advantage that this structure of the current limiter 944 can be embedded in known electrode conductor structures. For example, a particularly good contact can be made to a spiral-shaped functional lead, such as the functional lead 526 in FIG. 5A.

Mechanical loads can be borne by the stable electrode conductor itself when this geometry is used, while at the same time the semiconductor chip, which is sensitive to mechanical loading, is free of loading.

One variation of the embodiment involves a configuration where this mechanical rigidity is embodied in the tip spiral. As such, mechanical loads incurred upon placing the spiral into the tissue are not transferred to the sensitive semiconductor component, but rather can be transmitted by the configuration via a mechanically stable structure.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implantable medical device comprising:
at least one functional lead which extends longitudinally and is connected on a distal end thereof to an electrode pole that is configured to discharge therapeutic signals or detect diagnostic signals;
wherein said at least one functional lead comprises a current limiting device including a parallel circuit having a first current branch in parallel with a second current branch, the first current branch including a first current limiter and not a second current limiter and the second current branch including the second current limiter and not the first current limiter, wherein said first and second current limiter are configured to prevent electrical current in the at least one functional lead from exceeding a pre-specified maximum value; and,
wherein the first and second current limiter are switched to cause the second current limiter to function as a substitute of the first current limiter, when a strength of electrical current falls to a value lower than a pre-specified minimum value in the first current branch of the parallel circuit.

2. The implantable medical device according to claim 1, wherein electrical conductivity of the first current limiter is dependent either on a frequency of an alternating field to which the first current branch is exposed, or on an electrical voltage that occurs on the first current branch, or on a magnitude or a direction of an electric or magnetic field to which the first current branch is exposed, or on a temperature at the first current branch, or any combination thereof.

3. The implantable medical device according to claim 1, wherein the first current limiter comprises at least one diode or at least one transistor, or a circuit comprising at least one diode and at least one transistor.

4. The implantable medical device according to claim 3, wherein the at least one transistor comprises a junction gate field effect transistor or JFET, a metal-semi-conductor field effect transistor or MESFET, a field effect transistor with high electron movement or HEMT, or a metal oxide semiconductor field effect transistor or MOSFET.

5. The implantable medical device according to claim 3, wherein the first current limiter comprises two transistors switched in series, wherein gate electrodes thereof are directly connected to each other.

6. The implantable medical device according to claim 1, wherein the at least one functional lead comprises a plurality of longitudinal sections that possess higher or lower electrical conductivity with respect to each other, and wherein the second current limiter comprises a longitudinal section of lower electrical conductivity.

7. The implantable medical device according to claim 1, wherein the first current limiter comprises a monolithically integrated semiconductor component that includes a hollow cylinder having contact surfaces on ring-shaped longitudinal ends, wherein said hollow cylinder surrounds the at least one functional lead.

8. The implantable medical device according to claim 6, wherein the first current limiter comprises a monolithically integrated semiconductor component that includes a hollow cylinder having contact surfaces on ring-shaped longitudinal ends, wherein said hollow cylinder surrounds the at least one functional lead and surrounds the longitudinal section having lower electrical conductivity.

9. The implantable medical device according to claim 1, further comprising a control device, wherein the at least one functional lead comprises a connection device on a proximal end of its longitudinal extension that is configured to connect to the control device, and wherein the current limiting device is arranged near the distal end of the at least one function lead.

10. The implantable medical device according to claim 1, wherein the at least one functional lead is connected to contact bridges which are arranged on both sides of the current limiting device in a longitudinal direction, and which are configured to be directly connected to each other via a bridging device.

11. The implantable medical device according to claim 1, further comprising:
a control device which is connected to the at least one functional lead, and which comprises:
a measuring unit comprising a sensor which is configured to determine a measured value from varying strength of the electric current in the at least one functional lead ;
an analysis unit which is configured to detect an event where the electric current strength exceeds a pre-specified maximum value, and optionally to generate a control signal; and,
a switch unit that is connected to the first current limiter, and which is configured to produce a blocking voltage based on the control signal, wherein said blocking voltage blocks a first current branch leading through the first current limiter.

12. The implantable medical device according to claim 11, further comprising a therapeutic unit which is connected to the analysis unit, and which is configured to:
produce electrical stimulation impulses having a pre-specified temporal progression of amplitude thereof, wherein said impulses have a pre-specified target value of electrical current strength in the at least one functional lead wherein said pre-specified target value is larger than a minimum value and smaller than a maximum value;
discharge said stimulation impulses via the at least one functional lead to the external environment; and,
modify the pre-specified temporal progression of the amplitude in the at least one functional lead based on the control signal produced by the analysis unit.

13. The implantable medical device according to claim 11, wherein
the measuring unit is configured to detect an updated value of a parameter to display efficacy or lack of efficacy of stimulation impulses discharged into tissue;
the analysis unit is configured to detect the efficacy or lack of efficacy of the discharged stimulation impulses through use of the updated value and pre-specified criteria; and,
the therapeutic unit is configured to modify the pre-specified temporal progression of amplitude in the at least one functional lead when the lack of efficacy is detected.

14. The implantable medical device according to claim 11, wherein the sensor is arranged on the at least one functional lead and connected to the analysis unit via a second current branch leading through the second current limiter.

15. The implantable medical device according to claim 11, further comprising a communication unit configured to communicate between the implantable medical device and an external monitoring device on a communication channel wherein the communication unit is connected to the analysis unit, and wherein the communication unit is configured to signal the monitoring device when the control signal is present and on the same communication channel that an electrical current strength is present which exceeds the maximum value in the at least one functional lead.

* * * * *